(12) United States Patent
Brovelli et al.

(10) Patent No.: US 6,793,946 B2
(45) Date of Patent: Sep. 21, 2004

(54) COMPOSITION AND METHOD FOR LOWERING CHOLESTEROL

(75) Inventors: Ernesto A. Brovelli, Corona, CA (US); Julio Andres Vallejos, Corrientes (AR); Haeri Roh-Schmidt, Ada, MI (US)

(73) Assignee: Access Business Group International LLC., Ada, MI (US)

( * ) Notice: Subject to any disclaimer, the term of this patent is extended or adjusted under 35 U.S.C. 154(b) by 0 days.

(21) Appl. No.: 10/209,021

(22) Filed: Jul. 31, 2002

(65) Prior Publication Data

US 2004/0022883 A1 Feb. 5, 2004

(51) Int. Cl.$^7$ .............................................. A61K 35/78
(52) U.S. Cl. ...................................... 424/775; 424/774
(58) Field of Search .............................. 424/725, 195.1, 424/774

(56) References Cited

U.S. PATENT DOCUMENTS

| | | | | |
|---|---|---|---|---|
| 4,706,407 A | * | 11/1987 | Melton | ........................... 43/69 |
| PP6,627 P | * | 2/1989 | Coffey et al. | |
| 5,683,736 A | * | 11/1997 | Lunder | ....................... 426/597 |
| 6,129,924 A | | 10/2000 | Maurel | |
| 6,190,720 B1 | | 2/2001 | Yuan et al. | |
| 6,267,963 B1 | | 7/2001 | Akashe et al. | |
| 6,303,803 B1 | | 10/2001 | Kodali | |

FOREIGN PATENT DOCUMENTS

JP          8-332061          12/1996

OTHER PUBLICATIONS

Brown, T. Tom Brown's Guide to Wild Edible and Medicinal Plants; 1985, Berkley Publishing, New York, NY, p. 32.*
Morton, J. Fruits of Warm Climates; 1987, Miami Fl., pp. 91–102.*
Scora et al. Essential Oils of Persea Subgenus Persea (Lauraceae); J. Essent. Oil Res., 12, 2000, pp. 709–713.*
Effects of a Vegetarian Diet vs. a Vegetarian Diet Enriched with Avocado in Hypercolesterolemic Patients, Carranza–Madrigal J; Herrera–Abarca J E; Alvizouri–Munoz M; Alvarado–Jimenez Mr; Chavez–Carbajal F.; Archives of Medical Research, (1997 Winter) 28 (4) 537–41. Abstract.
Comparison of the Effects on Lipoproteins and Apolipoproteins of Diet High in Monounsaturated Fatty Acids, enriched with Avocado, and a High–carbohydrate Diet; Colquhoun D M; Moores D; Somerset S M; Humpries J A, American Journal of Clinical Nutrition, (Oct. 1992) 56 (4) 671–7. Abstract.
Effects of Avocado as a Source of Monounsaturated Fatty Acids on Plasma Lipid Levels, Alvizouri–Munoz M; Carranza–Madrigal J; Herrera–Abarca J E; Chavez–Carbajal F; Amezcua–Gastelum JL, Archives of Medical Research, (1992 Winter) 23 (4) 163–7. Abstract.
Monounsaturated Fatty acid (avocado) Rich \Diet for Mild Hypercholesterolemia; Lopez Ledesma R; Frati Munari A C; Hernandez Dominguez B C; Cervantes; Montal Vo S; Hernandez Luna M H; Juarez C; Moran Lira S., Archives of Medical Research, (1996 Winter)27 (4) 519–23. Abstract.
Effects of Avocado on the Level of Blood Lipids in Patients with Phenotype II and IV Dyslipidemas; Carranza J; Alvizouri M; Alvarado M R; Chavez F; Gomez M; Herrera JE, Archivos Del Instituto De Cardiologia De Mexico, (Jul.–Aug. 1995) 65 (4) 342–8. Abstract.
Effect of High–monounsaturated Fat Diet enriched with Avocado in NIDDM Patients Lerman–Garber I; Ihazo–Cerro S; Zamora–Gonzalez J; Cardoso–Saldana G; Posadas–Romero C;, Diabetes Care, (Apr. 1994) 17 (4) 311–5. Abstract.
Avocado Oils and Hepatic Lipid Metabolism in Growing Rate; Werman M J; Neeman I; Mokady S, Food and Chemical Toxicology, (Feb. 1991) 29 (2) 93–9. Abstract.
Influence of the Daily Ingestion of a Total Unsaponifiable Extract from Avocado and Soy Bean Oils on Cholesterol Metabolism in the Rat, Chevallier F; Lutton C; Sulpice J C; D'Hollander F. Pathologie Biologie, (Mar. 1975) 23 (3) 225–30. Abstract.
Avocados Protect Liver: Going Nuts—A Guide to the Wonderfully Nutritoous World of Nuts; Dr. Stephen Byrnes, (http://powerhealth.net/archivmidm rch2001.htm), reprinted from Ralph Moss' Newsletter at http://www.cancerdecisions.com.

* cited by examiner

*Primary Examiner*—Patricia Leith
(74) *Attorney, Agent, or Firm*—Amy I. Ahn; Alticor Inc.

(57) ABSTRACT

The present invention relates to a composition comprising *Persea american* var. *drymifolia* for lowering cholesterol levels.

7 Claims, 3 Drawing Sheets

COMPOSITION AND METHOD FOR LOWERING CHOLESTEROL

FIELD OF THE INVENTION

The present invention relates to compositions and methods for lowering cholesterol. More particularly, the present invention relates compositions and methods having avocado leaf of the species Persea americana var. drymifolia (hereinafter referred to as "drymifolia") for use in lowering cholesterol levels in humans.

BACKGROUND OF THE INVENTION

Cholesterol is a soft, waxy substance found among the lipids in the bloodstream and in cells of the human body. Although cholesterol serves needed bodily functions, too high a level of cholesterol in the blood may be detrimental to a person's health because it increases the risk of cardiovascular disease. High cholesterol generally means that a person's total blood cholesterol level is more than 240 mg/dl or that a person's low density lipoprotein level is more than 160 mg/dl (see, Cleeman, James I., Executive Summary of the Third Report of the National Cholesterol Education Program (NCEP) Expert Panel on Detection, Evaluation, and Treatment of High Blood Cholesterol in Adults (Adult Treatment Panel III), JAMA 285(19): 2486–2497 (2001)). Approximately 41.3 million Americans have total blood cholesterol levels of 240mg/dL or higher (see, American Heart Association, Biostatistical Fact Sheet, www.americanheart.org (2002)). When blood cholesterol reaches these high levels, it can build up on artery walls because cholesterol does not dissolve in the blood. Rather, cholesterol has to be transported to and from the cells by special carriers called low-density lipoproteins (LDL) and high density proteins (HDL). HDL carries cholesterol away from your arteries and is, thus, considered "good cholesterol." Too much LDL cholesterol can clog the arteries to your heart and is, thus, considered "bad cholesterol." This condition, called atherosclerosis, increases the risk of blood clots, heart attack, and stroke.

Accordingly, there is considerable amount of interest in regulating cholesterol level in the body. There are several classes of available lipid-regulating pharmacological interventions called statins. One common statin is LIPITOR®. Although these agents have been proven safe in clinical trials, like any drug, they carry the risk for side-effects. Most notable of the side-effects is myopathy, which becomes evident as muscle pains and weakness. Furthermore, it is important to minimize the potential for adverse reactions or drug interactions when a patient is undergoing statin therapy (see, Davidson, Michael H., Treatment of the Elderly with 3-Hydroxy-3-Methylglutaryl Coenzyme A Reductase Inhibitors: Focus on Drug Interactions, J Cardiovasc Pharmacol Therapeut, 6(3): 219–229 (2001)). In its Adult Treatment Panel, the National Cholesterol Education Program recommends the use of plant derived substances in the adjuvant therapies for dyslipidemias (see Cleeman, supra). Accordingly, natural alternatives with effective and safe cholesterol reduction are desired.

SUMMARY OF THE INVENTION

The present invention is a composition containing avocado leaves from the variety drymifolia for reducing cholesterol levels. In one embodiment the leaves are dehydrated and milled for consumption as a tea. Surprisingly, the leaves of drymifolia showed a comparable cholesterol lowering effect to LIPITOR® and a much greater cholesterol lowering effect than the fruit and the leaves of Persea nubigena var. guatamalensis cv. Nabal and Persea nubigena var. guatamalensis cv. Haas, which are avocados commonly grown in North America.

These and other aspects and advantages of the present invention will be better understood by reference to the drawings and the detailed description of the preferred embodiment. It is noted that, unless otherwise stated, all percentages given in this specification and the appended claims refer to percentages by weight.

DETAILED DESCRIPTION OF THE PREFERRED EMBODIMENT

Figure 1:
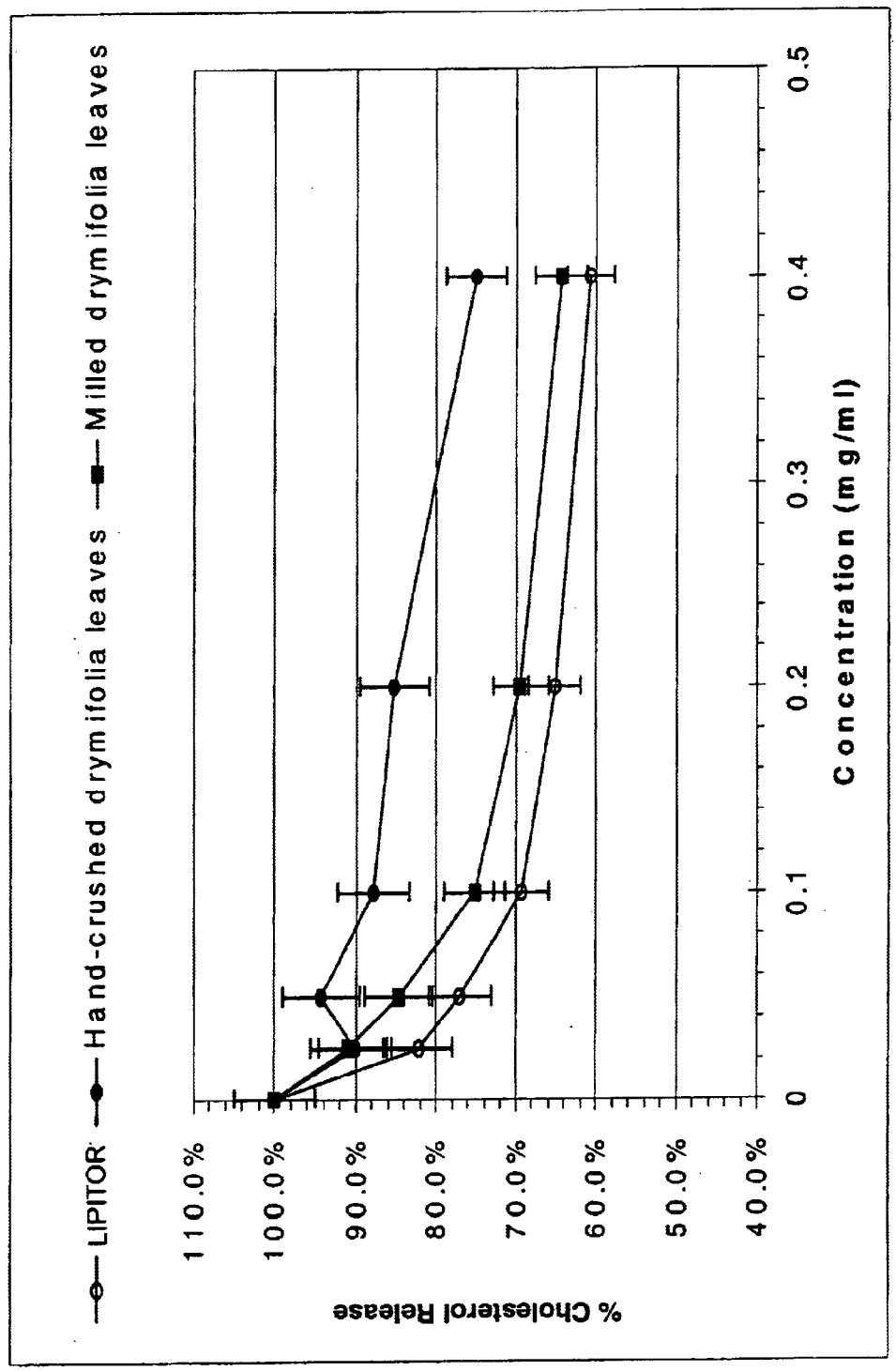
FIG. 1 is a graph displaying dose specific responses of Hepatocyte G2 cells to hand-crushed and milled leaves of drymifolia in comparison to LIPITOR® in cholesterol release.

The present invention comprises avocado leaves from the variety Persea americana var. drymifolia ("drymifolia"). This variety is available in Northern Argentina. The particular substance(s) in the leaves that causes cholesterol lowering is not yet understood. However, it is a commonly understood principle in the herbal industry that active ingredients in fresh plants/herbs generally decompose or diminish in effectiveness as the plant/herb dies or decays. Thus, to preserve the cholesterol reducing capacity of the drymifolia leaves for shipment from Argentina to the United States, the fresh drymifolia leaves are preferably air dried at average room temperatures of about 60° F. to about 80° F. This temperature range is maintained until the leaves are prepared for consumption. Surprisingly, this preconditioning step maintains the efficacy of the drymifolia leaves in lowering cholesterol.

Once dehydrated, the leaves are preferably hand-crushed. The hand-crushed leaves showed better cholesterol lowering activity than the fruit and leaves of Persea nubigena var. guatamalensis cv. Nabal ("Nabal") and the leaves of Persea nubigena var. guatamalensis cv. Haas ("Haas"). More preferably, dehydrated leaves are milled using a 2 mm screen to mill the leaves to an average particle size of about 28 microns. Even more preferably, the leaves may be milled twice using a 1 mm screen to provide an average particle size of about 9 microns. Most preferably, the dehydrated leaves may be milled using a 1 mm screen, providing an average particle size of about 11 microns. Milling can be performed by a GlenMills hammer mill bench top unit (Mot. KM 80-60, Culatti Typ MFC). Milled drymifolia leaves showed greater cholesterol reduction than hand-crushed drymifolia leaves. It is contemplated that the milled and dehydrated leaves can be used in the form of tea, capsules, tablets, creams, gels, liquids, and foods. However, for exemplary purposes, preparation and consumption in the form of a tea is described.

The tea is prepared as a 1% extract by preparing 10 mg of hand-crushed *drymifolia* leaves or milled *drymifolia* leaves per 1 ml of water. In one embodiment, 100 mg of *drymifolia* leaves are placed in 10 ml of water to form a tea. The tea is boiled for about 1 minute to about 10 minutes. More preferably, the tea is boiled for about 3 minutes to about 7 minutes and, most preferably, for about 5 minutes. The water can be boiling after or upon immersing the *drymifolia* leaves in the water. It will be appreciated by those of ordinary skill in the art that the boiling times will vary depending upon the volume of the tea.

*Drymifolia* Comparison Studies

To test the efficacy of the *drymifolia* tea containing milled *drymifolia* leaves having an average particle size of about 11 microns, comparison studies were performed with tea containing hand-crushed *drymifolia* leaves, LIPITOR®, Haas fruit, and milled leaves of Haas and Nabal having an average particle size of about 11 microns. LIPITOR® is prepared in methanol/buffer to solubilize atorvastatin, the active ingredient in LIPITOR® (40 mg active/600 mg tablet). All test materials were applied to serum culture medium at varying doses.

Tea containing *drymifolia* leaves having an average particle size of about 11 microns was added to Dulbecco's Modified Eagle Medium (DMEM, Catalogue #11965, In Vitrogen Corporation, 1600 Faraday Avenue, P.O. Box 6482, Carlsbad, Calif. 92008) to a final concentration of about 0.1 mg/ml to about 0.5 mg/ml *drymifolia* leaves via serial dilution (or 0.01% to 0.05% *drymifolia* leaves). More preferably, the final concentration is about 0.2 mg/ml to about 0.4 mg/ml *drymifolia* leaves and, most preferably, about 0.4 mg/ml *drymifolia* leaves. The culture media provides all necessary nutrients for cell maintenance including cholesterol synthesis.

| Components of Culture Medium | Molarity (mM) |
|---|---|
| INORGANIC SALTS: | |
| Calcium Chloride (CaCl2) (anhyd.) | 1.80 |
| Ferric Nitrate (Fe(NO3)3–9H2O) | 0.000248 |
| Potassium Chloride (KCl) | 5.30 |
| Magnesium Sulfate (MgSO4) | 0.813 |
| Sodium Chloride (NaCl) | 110.34 |
| Sodium Bicarbonate (NaHCO3) | 44.10 |
| Sodium Phosphate (NaH2PO4–H2O) | 0.906 |
| OTHER COMPONENTS: | |
| D-Glucose | 25.00 |
| Phenol red | 0.0346 |
| AMINO ACIDS: | |
| L-Arginine-HCl | 0.398 |
| L-Cystine 2HCl | 0.200 |
| L-Glutamine | 4.00 |
| Glycine | 0.399 |
| L-Histidine HCl–H2O | 0.20 |
| L-Isoleucine | 0.802 |
| L-Leucine | 0.802 |
| L-Lysine-HCl | 0.798 |
| L-Methionine | 0.201 |
| L-Phenylalanine | 0.400 |
| L-Serine | 0.400 |
| L-Threonine | 0.078 |
| L-Tryptophan | 0.078 |
| L-Tyrosine 2Na 2H2O | 0.398 |
| L-Valine | 0.803 |

-continued

| Components of Culture Medium | Molarity (mM) |
|---|---|
| VITAMINS: | |
| D-Ca pantothenate | 0.0083 |
| Choline Chloride | 0.0285 |
| Folic Acid | 0.00906 |
| i-Inositol | 0.04 |
| Niacinamide | 0.0328 |
| Pyridoxine HCl | 0.0196 |
| Riboflavin | 0.00106 |
| Thiamine HCl | 0.0118 |

Amounts of secreted cholesterol and cholesteryl ester were measured from acetate fed hepatocyte culture media using a fluorescent indicator, AMPLEX RED. As shown in FIG. 1, it is apparent that the effect of milled *drymifolia* leaves is comparable to that of LIPITOR®. The results also show that milled *drymifolia* leaves with an average particle size of about 11 microns had a more favorable result than that of hand-crushed *drymifolia* leaves when water extracts are made from each. The response of hepatocytes also indicated little or no toxicity associated with the doses treated when cell survival post treatment was assessed via MTT (3-[4,5-dimethylthiazol-2yl]-2,5-diphenyltetrazolium bromide, Sigma, St. Louis, Mo.) reduction assay.

Figure 2:
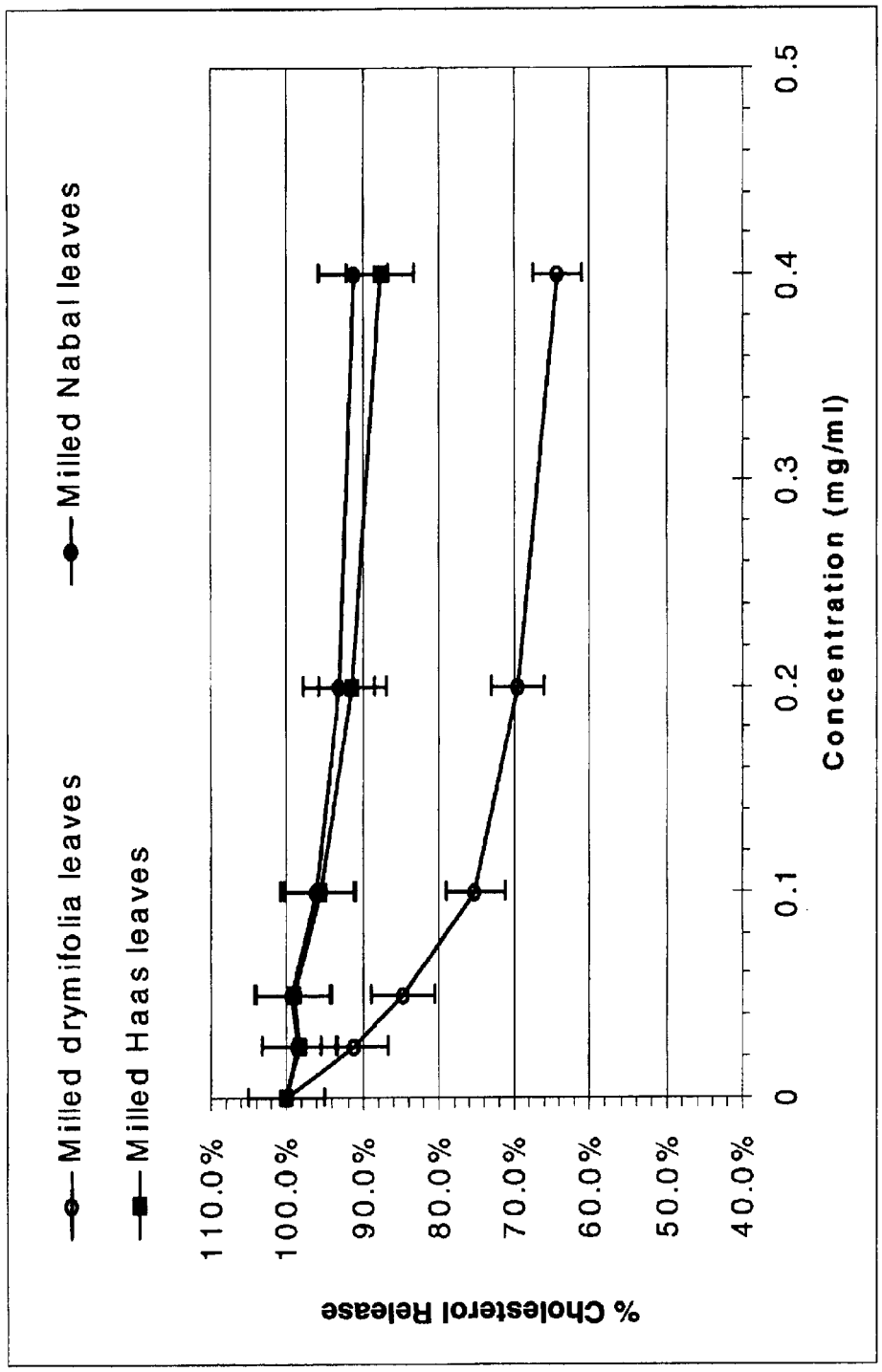
FIG. 2 is a graph displaying dose specific responses of Hepatocyte G2 cells to milled leaves of drymifolia in comparison to milled leaves of Persea nubigena var. guatamalensis cv. Nabal and milled leaves of Persea nubigena var. guatamalensis cv. Haas in cholesterol release.

FIG. 2 shows the effect of the milled *drymifolia* leaves to milled leaves of Haas and Nabal. FIG. 2 shows that *drymifolia* leaves have a more favorable effect in decreasing cholesterol synthesis/secretion than that of Haas or Nabal.

Figure 3:
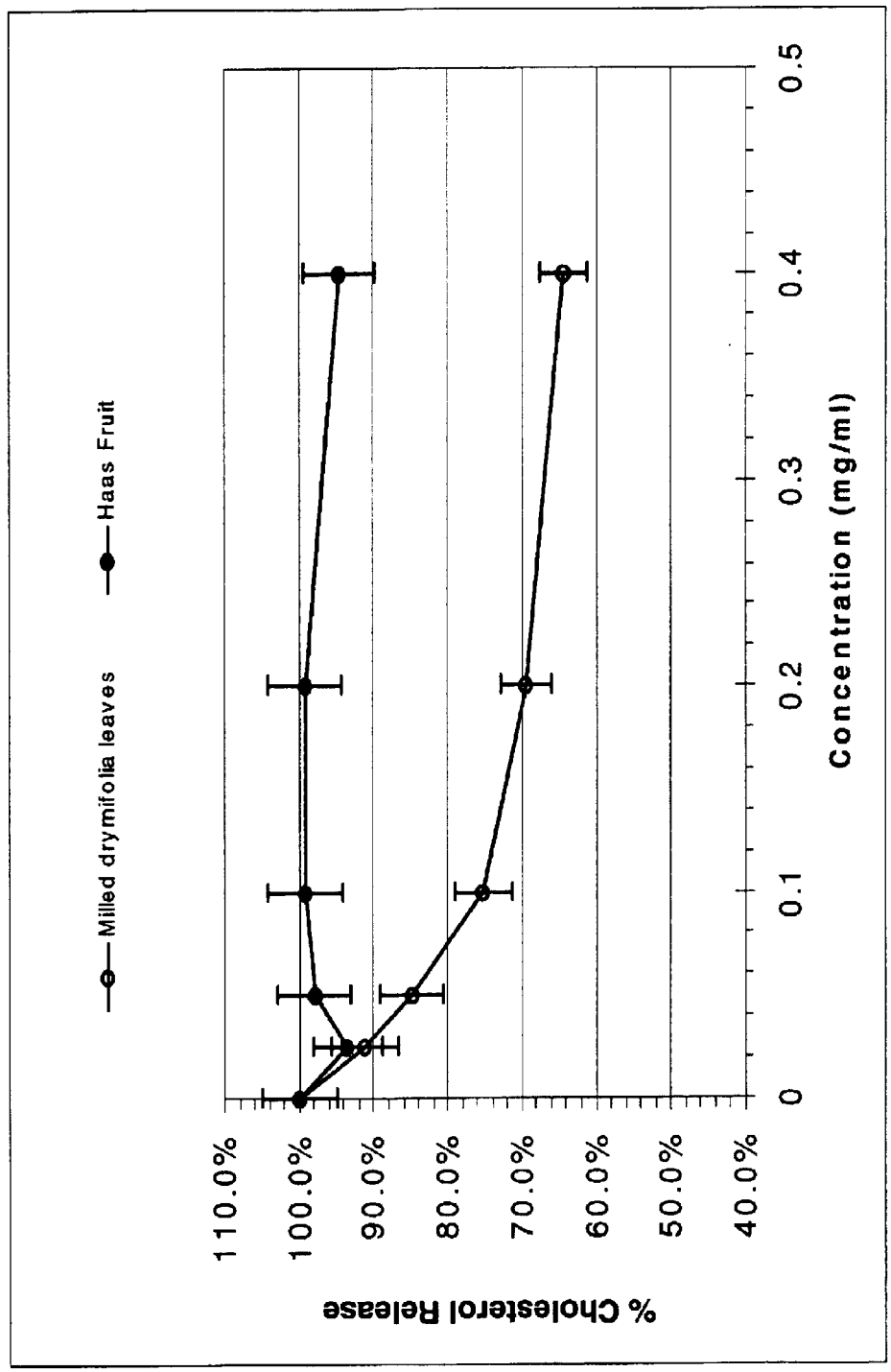
FIG. 3 is a graph displaying dose specific responses of Hepatocyte G2 cells to milled leaves of drymifolia in comparison to the fruit of Persea nubigena var. guatamalensis cv. Haas in cholesterol release.

As shown in FIG. 3, when the cholesterol inhibitory effect of Haas fruit is assessed in comparison to that of the milled *drymifolia* leaves, the milled leaves again exerted much more favorable response than the fruit.

While the above describes what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed:

1. A composition for lowering cholesterol levels comprising about 0.01% to about 0.05% of *Persea americana* var. *drymifolia* leaves by total weight of said composition wherein said *drymifolia* leaves have an average particle size of about 9 microns to about 28 microns.

2. The composition of claim 1 wherein said composition is a beverage containing *drymifolia* leaves.

3. The composition of claim 1 wherein said composition is a dietary supplement.

4. The composition of claim 1 wherein said composition lowers total blood cholesterol levels by about 10% to about 40%.

5. The composition of claim 1 wherein said *Persea americana* var. *drymifolia* leaves have an average particle size of about 11 microns.

6. The composition of claim 1 wherein said *Persea americana* var. *drymifolia* leaves are present in the amount of about 0.04% by total weight of said composition.

7. A tea for lowering cholesterol levels comprising about 0.1 mg/ml to about 0.5 mg/ml of *Persea americana* var. *drymifolia* leaves.

* * * * *